United States Patent [19]
Johnson, Jr. et al.

[11] Patent Number: 5,277,695
[45] Date of Patent: Jan. 11, 1994

[54] ADJUSTABLE ANKLE COMPRESS

[75] Inventors: Glenn W. Johnson, Jr., Summit; Henry J. McVicker, Chatham, both of N.J.

[73] Assignee: Aircast, Inc., Summit, N.J.

[21] Appl. No.: 789,749

[22] Filed: Nov. 8, 1991

[51] Int. Cl.$^5$ .............................................. A61F 5/00
[52] U.S. Cl. ........................................ 602/14; 602/27; 602/65; 128/DIG. 20; 607/111; 607/104
[58] Field of Search ........ 128/400, 402, 403, DIG. 20; 602/14, 27, 65, 16

[56] References Cited
U.S. PATENT DOCUMENTS 4,401,113  8/1983  Incorvaia .............................. 602/65
4,771,768  9/1988  Crispin ................................. 602/16
4,844,094  7/1989  Grim .................................... 602/27
5,007,416  4/1991  Burns et al. ........................ 128/403
5,088,478  2/1992  Grim .................................... 128/402

Primary Examiner—Richard J. Apley
Assistant Examiner—Lynne A. Reichard
Attorney, Agent, or Firm—Jones, Day, Reavis & Pogue

[57] ABSTRACT

An adjustable ankle compress (10) in the shape of a boot (12) with an ankle portion (18) and a foot portion (16) for receiving the ankle and foot and having a sole (14) on the boot (12) that is adjustable in width for varying the size of the boot (12) to accommodate a foot and ankle of various sizes. The boot (12) has a fluid-tight compartment (36) formed therein for substantially surrounding the ankle and the top of the foot.

1 Claim, 4 Drawing Sheets

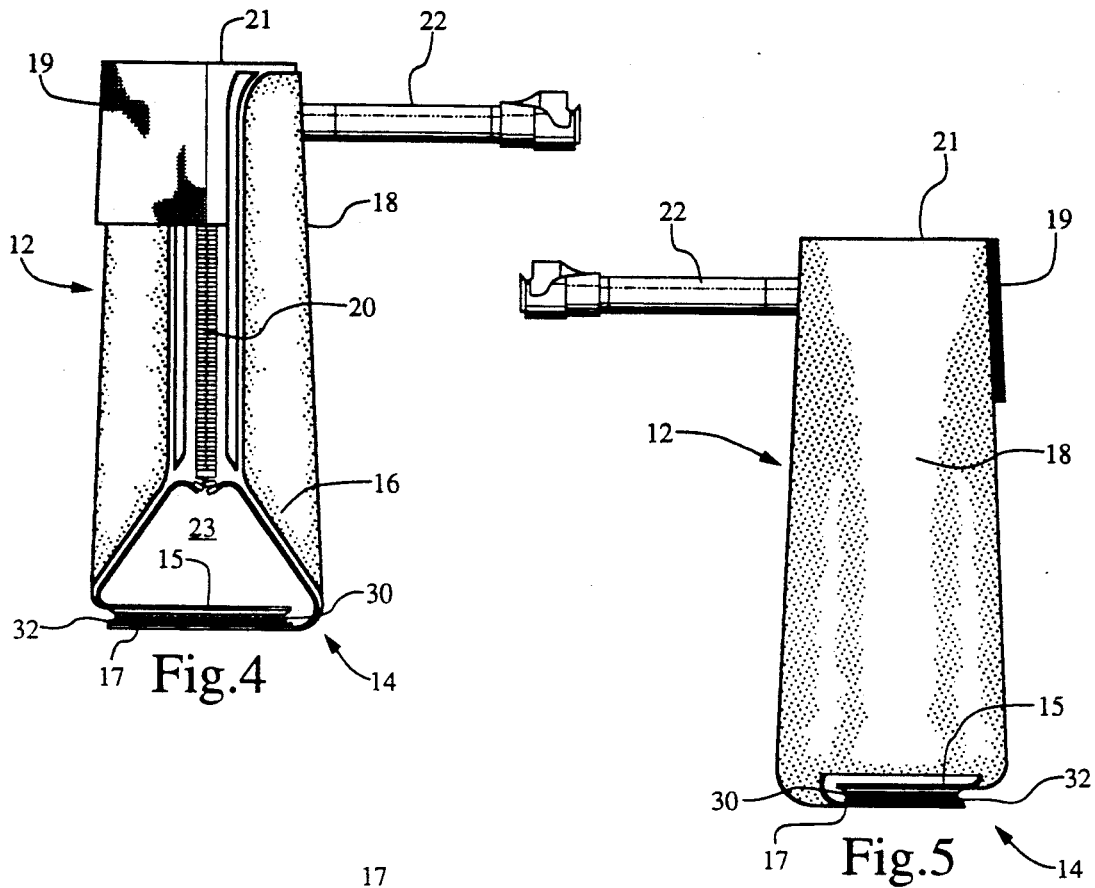
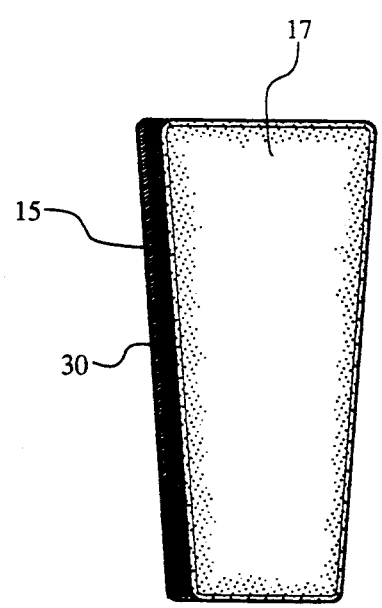
Fig.4  Fig.5
Fig.6  Fig.7

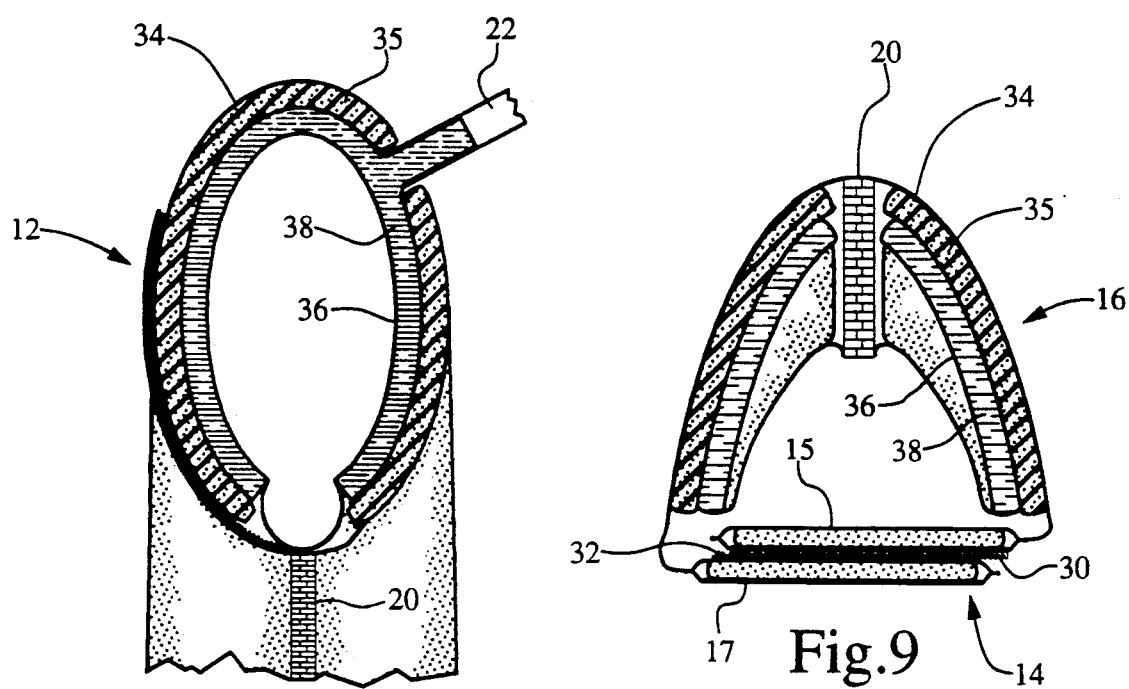

ADJUSTABLE ANKLE COMPRESS

FIELD OF THE INVENTION

This invention relates to a compress used in the application of heat or cold to an injured foot or ankle of the human body. In particular, the invention relates to an ankle compress for applying hot or cold temperatures to the ankle and foot of the human body and which is adjustable in size to provide a proper fit for an injured ankle and foot.

BACKGROUND OF THE INVENTION

The human ankle and foot may be injured by sprains, contusions, bruises, degenerative joint diseases, arthritis, and arthroscopic operations. Such injuries may cause hematomas and inflamed areas that need to be treated. In such cases, it has been found advantageous to apply a compress of some type to the injured area to effect more rapid healing. In some cases, the compress may include a cold, or sometimes hot, substance. Where a cold substance is required, ice packs have been used and more recently a compress of some type has been used that is filled with a cold liquid and the compress is then applied to the injured area. Some devices, such as that disclosed in U.S. Pat. No. 3,900,035, form an elastic bandage for an ankle. The bandage has a shape to receive a foot and has a plurality of liquid pockets embedded in the elastic bandage to fit tightly to the foot and around the ankle. The pockets are filled with a material that can be cooled or heated.

A number of liquid filled devices of the prior art are in a form generally as rectangular bladders or U-shaped bladders which have either a filling cap through which the liquid is inserted or which has the liquid permanently sealed inside a cavity. With each of these devices, it is difficult to secure the bladder properly to the affected area so that proper healing can take place. Further, some of these devices have straps at fixed angles and yet have to accommodate many different sizes of ankles. Friction points result in some circumstances because the straps must be flexed to adjust an angle. Further, fixed straps do not always allow for complete overlap of Velcro areas and the exposed Velcro may rub against an outer garment and is a source of irritation.

Also, some of the prior art devices allow the liquid therein to be frozen by placing the device filled with the liquid in a conventional freezer compartment. The frozen package is then attached to the affected part of the body. These devices are disadvantageous because the frozen liquid prevents the bag from conforming to the shape of the affected area. Other devices have a relatively thin bladder which allows the layer of ice to be broken into smaller particles so that the bladder can be shaped to the area against which it is placed.

While the above-described devices illustrate a steady improvement in the art for treatment of ankle injuries, they are still lacking in many respects. For instance, there is still a problem with getting a thermal compression device to adequately contact the injured area of the body in a uniform manner. Also, it is desirable to vary the compression depending upon the injury being treated.

The present invention relates to an improved ankle sprain management system including a thermal compress in the shape of a boot that may be used to treat an injured ankle. The improved boot-shaped thermal compress is adjustable to accommodate a foot and ankle of various sizes. The boot-shaped body has an ankle portion and a foot portion for receiving the ankle and foot. A sole on the boot is adjustable in width for varying the size of the boot-shaped body to accommodate various size ankles and feet. The adjustable sole has an inner portion pivotally attached to one side of the bottom of the boot-shaped body and an outer portion pivotally attached to the other side of the bottom of the boot-shaped body and overlapping the inner portion. Hooks and loops mounted on the overlapping portions of the inner and outer sole portions allow the outer portion to overlap the inner portion in any desired amount so as to adjust the width of the boot. The novel boot contains a fluid-tight compartment for substantially surrounding the ankle and the top of the foot. It has closable access means coupled to the compartment for allowing a fluid of predetermined temperature to be entered into the compartment for aiding and treatment of the foot and ankle. An open toe is formed in the foot portion of the boot-shaped body and an elongated opening extends from the top of the front of the boot-shaped body to the open toe to facilitate placement of the foot in the boot-shaped body. A zipper closes the opening after the foot is inserted in the boot. A container holds a liquid such as ice water and a hose or conduit couples the container to the closable access means to enable the liquid from the container to enter the compartment in the boot-shaped body.

Thus, it is one aspect of the present invention to provide an adjustable ankle compress in the shape of a boot that has a sole on the boot that is adjustable in width for varying the size of the boot to accommodate a foot and ankle of various sizes.

It is another aspect of the present invention to provide an adjustable ankle compress in the shape of a boot that has an adjustable sole with an inner portion pivotally attached to one side of the botom of the boot and an outer portion pivotally attached to the other side of the bottom of the boot and overlapping the inner portion with hook and loops mounted on the overlapping portions to allow the outer portion to overlap the inner portion in any desired amount so as to adjust the width of the boot.

It is also an aspect of the present invention to provide an adjustable ankle compress in the shape of a boot having a fluid-tight compartment formed in the boot for substantially surrounding the ankle and the top of the foot with closable access means coupled to the compartment for allowing a fluid of predetermined temperature to be entered into the compartment for aiding in treatment of the foot and ankle.

It is still another aspect of the present invention to provide an adjustable ankle compress in the shape of a boot having an open toe and having a zipper extending from the top of the front of the boot to the open toe to facilitate placement of the foot in the boot.

SUMMARY OF THE INVENTION

The present invention relates to an adjustable ankle compress comprising a boot-shaped body having an ankle portion and a foot portion for receiving the ankle and foot and a sole on the boot that is adjustable in width for varying the size of the boot-shaped body to accommodate a foot and ankle of various sizes.

BRIEF DESCRIPTION OF THE DRAWINGS

These and other objects of the present invention will be more fully disclosed in the following detailed description taken in conjunction with the drawings in which like numerals represent like elements and in which:

FIG. 4 is a front view of the novel adjustable ankle compress;

FIG. 5 is a rear view of the novel adjustable ankle compress;

FIG. 6 is a bottom view of the adjustable sole of the ankle compress in a first position;

FIG. 7 is a bottom view of the adjustable sole of the ankle compress in another position;

FIG. 8 is a cross-sectional view of the upper portion of the adjustable ankle compress taken along lines 8—8 of FIG. 2; and FIG. 9 is a cross-sectional view of the toe of the adjustable ankle compress taken along lines 9—9 of FIG. 2.

DETAILED DESCRIPTION OF THE DRAWINGS

Figure 1:
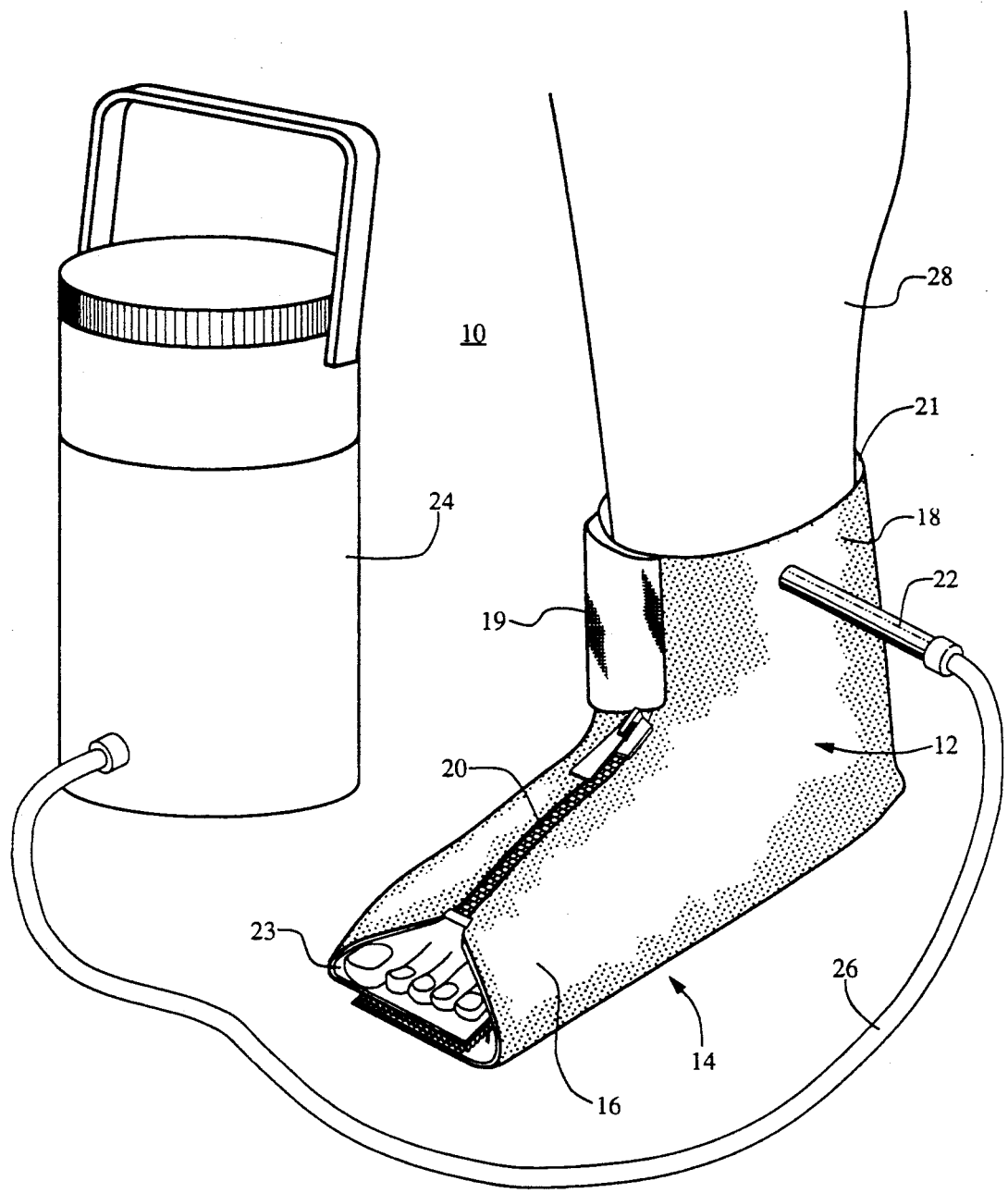
FIG. 1 is a schematic representation of the present adjustable ankle compress on a foot and attached to a liquid container.

FIG. 1 discloses the novel adjustable ankle compress system 10 including a boot-shaped body 12 having an adjustable width sole portion 14, a foot portion 16 and an ankle portion 18. An upper closure flap 19 is attached to the upper portion 18 and extends from the top 21 of the body 12 to the zipper 20. Zipper 20 extends from the bottom of the closure flap 19 to the open toe 23 to facilitate placement of a foot of a leg 28 in the boot-shaped body 12. A fluid-tight compartment 36 (shown in FIGS. 8 and 9) is formed in the boot-shaped body 12 for substantially surrounding the ankle and the top of the foot as will be seen hereafter. A closable fluid access means 22 is coupled to the compartment 36 in the boot 12 for allowing a fluid of predetermined temperature to be entered into the compartment from a container 24 through a hose or conduit 26 to aid in treatment of the foot and ankle.

Figure 2:
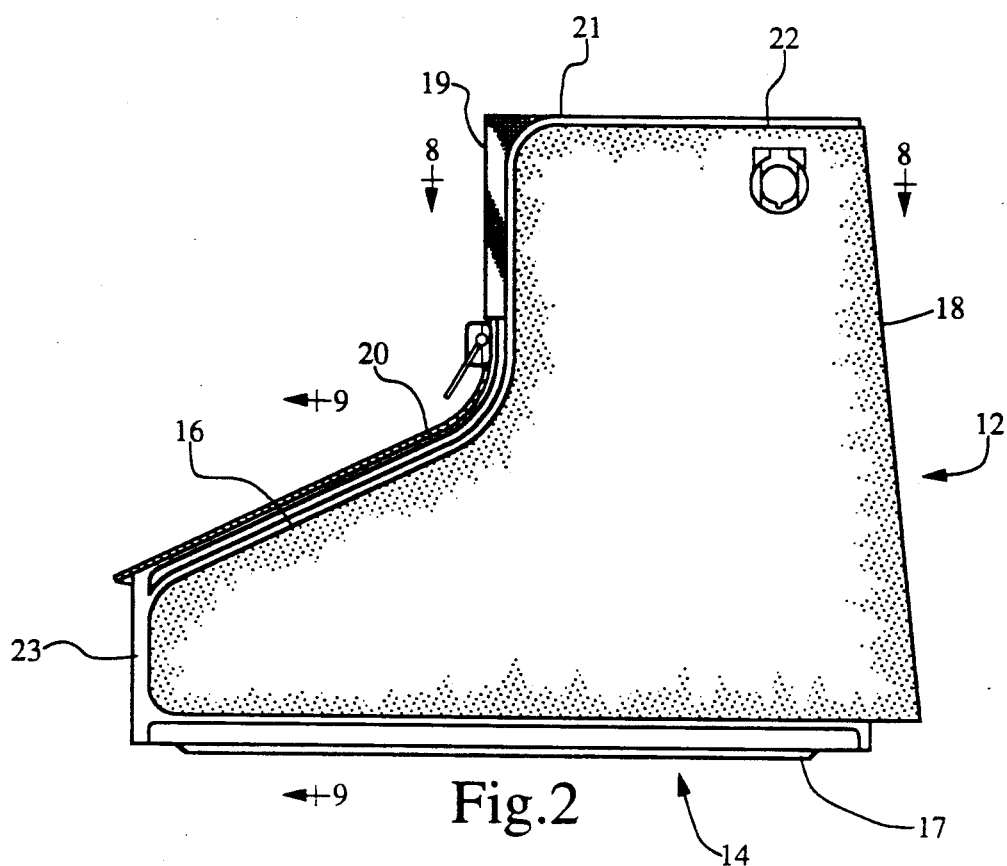
FIG. 2 is a side view of the novel adjustable ankle compress.
Figure 3:
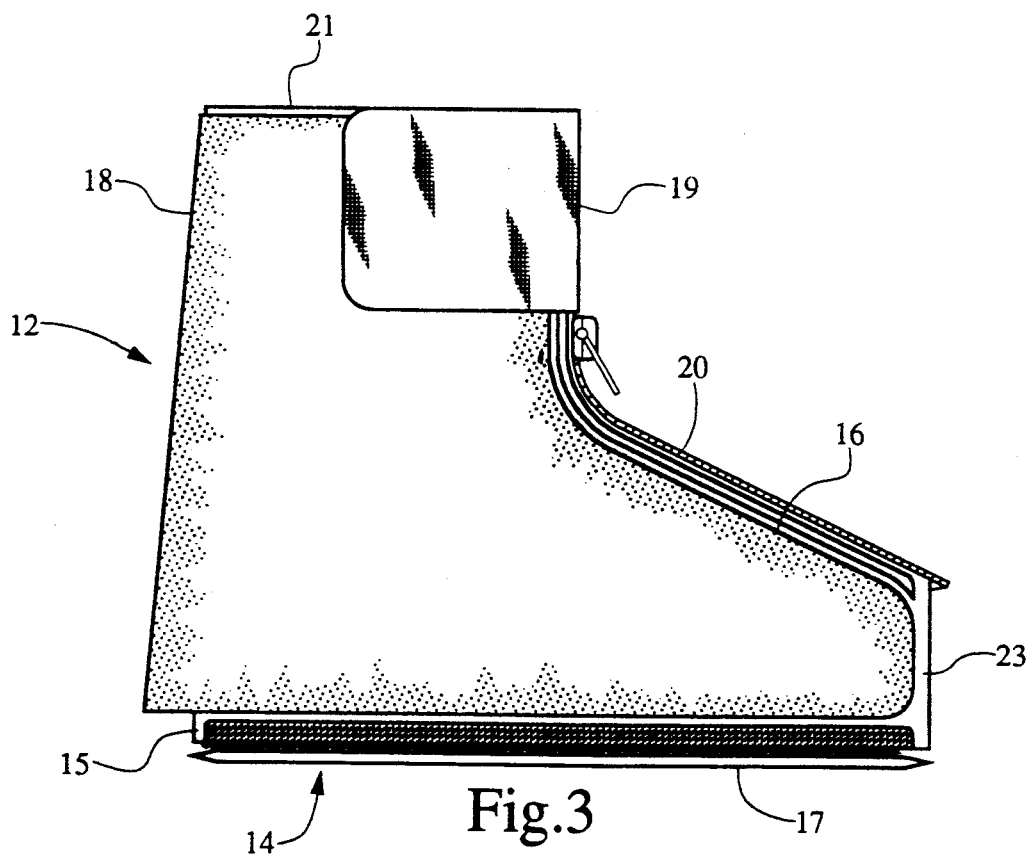
FIG. 3 is the opposite side view of the adjustable ankle compress.

FIGS. 2 and 3 are respective side views of the novel adjustable ankle compress in the shape of a boot 12. Shown in FIGS. 2 and 3 are the adjustable width sole 14, the toe portion 16 of the boot 12, the ankle portion 18, the zipper 20, the closable access means 22, the closure flap 19 attached to the upper portion 18 of the boot 12 and the open toe 23. It is necessary only to unzip the zipper 20, open the flap 19 and the front of the boot, insert the foot, close the front of the boot with the zipper 20 after the foot is inserted in the boot, attach the flap 19 with hooks and loops (or in any other well-known manner) and add chilled liquid or water of any other desired temperature to the compartment 36 through the closable access means 22. By lifting the container 24 above the boot 12 the pressure in the boot can be varied. The sole 14 of the boot is made adjustable by forming the sole 14 with an inner portion 15 pivotally attached to one side of the bottom of the boot 12 and an outer overlapping portion 17 pivotally attached to the other side of the bottom of boot 12. A hook and loop system 30 and 32 is formed on the overlapping portions as shown in FIGS. 4 and 5 of the inner 15 and outer 17 sole portions to allow the outer portion 17 to overlap the inner portion 15 in any desired amount so as to adjust the width of the sole 14 of the boot 12. This will be seen more clearly hereafter in relation to FIGS. 6 and 7.

FIGS. 4 and 5 are front and rear views, respectively, of the adjustable ankle compress boot 12. The ankle portion 18 is illustrated and the closable access means 22 is illustrated near the top 21 of the boot 12. The sole portion 14 illustrates the outer portion 17 overlapping the inner portion 15 and being held with the hooks and loops 30 and 32.

FIGS. 6 and 7 are bottom views of the novel adjustable thermal compress illustrating the sole portion 14 of the boot 12 with the outer portion 17 overlapping the inner portion 15. In FIG. 8, the outer portion 17 almost entirely overlaps the lower portion 15 and is held in place by the hook and loops 30, 32. In FIG. 9, the lower portion 17 of the sole 14 overlaps only a small portion of the inner sole 15, thus enabling the width of the sole to be greatly increased. This capability of enlarging the width of the sole 14 allows the boot 12 to be adjusted to a variety of sizes of feet and ankles as well as ankles that are swollen.

As can be seen in FIG. 8, a cross-sectional view of the upper portion of the boot 12 taken along lines 8—8 of FIG. 2, the boot 12 has an outer portion 34 that may be filled with, or is formed of, an insulating material 35 of any-well known type. A liquid-tight compartment 36 is formed on the inside of the outer material 34 to be insulated by the material 35. The inner liquid tight compartment 36 contains a liquid 38 that may be inserted therein through the closable access means 22. Because the fluid 38 substantially surrounds the ankle and the top of the foot, and because it is insulated by the insulating material 35, a fluid 38 that is chilled will maintain its lower temperature for a longer period of time and will force the thermal radiation from the fluid to the foot and ankle that the compartment 36 surrounds. As stated previously, the pressure in the compartment 36 can be varied by raising and lowering the container 24 shown in FIG. 1.

FIG. 9 is a cross-sectional view of the toe portion 16 of the boot 12 taken along lines 9—9 of FIG. 2. It will be noted in FIG. 9 that the inner compartment 36 substantially surrounds the top of the foot inserted in the boot 12. If desired, of course, the zipper 20 could be replaced with a hook and loop fastener such as a Velcro fastener which would allow the outer end portions of the liquid-tight compartment 36 to abut or overlap, thus totally surrounding the top of the foot. Also as can be seen in FIG. 9, a resilient pad 40, such as foam rubber, may be attached to the top of the inner portion 15 of the sole 14 to provide a cushion for the sole of the foot inserted in the boot 12. The hook and loops 30, 32, such as a product well known in the art and sold under the trade name Velcro, hold the lower portion 17 of the sole 14 attached to the upper portion 15. The upper closure flap 19 aids in providing an adjustable upper opening in which the foot can be inserted and then adjusted to fit the boot to the ankle.

Thus there has been disclosed a novel adjustable width compress comprising a boot-shaped body having an ankle portion and a foot portion for receiving the ankle and foot. A sole portion on the boot is adjustable in width for varying the size of the boot-shaped body to accommodate a foot and ankle of various sizes. The adjustable sole includes an inner portion pivotally attached to one bottom side of the boot-shaped body, an outer portion pivotally attached to the other bottom side of the boot-shaped body and overlapping the inner portion and hook and loop material on the overlapping portions of the inner and outer sole portions to allow the outer portion to overlap the inner portion in any desired amount so as to adjust the width of the boot. The boot has an inner fluid-tight compartment surrounded by an outer insulating material which maintains the fluid in the compartment at its initial temperature for prolonged periods of time. The fluid can be in a container that is coupled to the inner compartment of the boot through a hose and a closable access device and the pressure in the boot can be varied by raising and lowering the container of fluid to various heights above the boot.

While the invention has been shown and described with respect to a particular embodiment thereof, this is for the purpose of illustration rather than limitation; other variations and modifications of the specific embodiment herein shown and described will be apparent to those skilled in the art all within the intended spirit and scope of the invention. Accordingly, the patent is not to be limited in scope and effect to the specific embodiment shown and described nor in any other way that is inconsistent with the extent to which the progress in the art has been advanced by the invention.

We claim:

1. An adjustable ankle compress comprising:
   a body portion having an upper ankle enclosing portion and a lower foot enclosing portion for receiving the ankle and foot;
   a substantially flat sole on said foot enclosing portion that is adjustable in width, the substantially flat adjustable sole comprising:
      a substantially flat inner portion pivotally attached to and integrally formed with one side of the lower foot enclosing portion;
      a substantially flat outer portion pivotally attached to the other side of the lower foot enclosing portion and overlapping said inner portion; and
      hook and loop material on the overlapping portions of said inner and outer sole portions to allow the substantially flat outer portion to overlap the substantially flat inner portion in any desired amount so as to adjust the width of the boot sole;
   a fluid-tight compartment formed in said body portion for substantially surrounding said ankle and the top of said foot;
   closable access means coupled to said fluid-tight compartment for allowing a fluid of predetermined temperature to be entered in to said fluid-tight compartment for aiding in treatment of said foot and ankle;
   an open toe in the lower foot enclosing portion;
   an opening extending from the top of the front of the body portion to the open toe to facilitate placement of the foot and ankle in said body portion;
   an adjustable upper flap attached to the upper ankle enclosing portion and having attachment means for closing an upper portion of the opening; and
   a zipper extending down the front of the body portion from the adjustable upper flap to the open toe for closing the opening.

* * * * *